United States Patent [19]

Mirkin et al.

[11] 4,146,788

[45] Mar. 27, 1979

[54] METHOD AND APPARATUS FOR QUANTITATIVE STRUCTURAL ANALYSIS OF SOLIDS

[76] Inventors: Georgy R. Mirkin, ploschad Chernyshevskogo, 6, kv. 5, Leningrad; Nadezhda A. Rumyantseva, ulitsa Menzhinskogo, 13, korpus 1, kv. 19, Moscow; Vyacheslav N. Sokolov, Daev pereulok, 31, kv. 14, Moscow; Viktor I. Osipov, Universitetsky prospekt, 9, kv. 16, Moscow; Mikhail D. Tolkachev, ulitsa Marata, 65, kv. 6, Leningrad; Evgeny S. Romm, Nevsky prospekt, 109, kv. 3, Leningrad, all of U.S.S.R.

[21] Appl. No.: 859,449

[22] Filed: Dec. 12, 1977

[51] Int. Cl.$^2$ ............................................. G01M 23/00
[52] U.S. Cl. ..................................... 250/311; 250/253
[58] Field of Search ......................... 250/311, 255, 253

[56] References Cited

U.S. PATENT DOCUMENTS 4,031,391   6/1977   Hoppe ................................. 250/311

Primary Examiner—Harold A. Dixon
Attorney, Agent, or Firm—Lackenbach, Lilling & Siegel

[57] ABSTRACT

In the proposed method a solid specimen is cleaved to obtain a pair of conjugate cleavage surfaces. Then, a scanning electron microscope is used to obtain images of the conjugate surfaces at a predetermined magnification. The images are superimposed to produce an image of a porous component of the solid structure. Thereafter, the image of the porous component is superimposed on each image of the conjugate surfaces to obtain a pair of images of imprints of solid grains. The image of pores and grain imprints is then converted to a contour form, all converted images are superimposed, and a contour image of the entire structure of the solid is obtained. The images of pores, grain imprints and complete structure of the solid are quantitatively analyzed with the aid of image analyzers, digitized and fed into a computer for calculation of the solid properties of interest, e.g., perviousness, using an appropriate program. Then, the direction of optimum pore image readout, corresponding to the direction of the structure's anisotropy, is determined by its spatial spectrum.

The proposed method can be effective with an apparatus comprising a scanning electron microscope with a TV monitor, an image video recorder, an additional TV monitor with a signal brightnes control, a light pen for marking images on the screens of the TV monitors, to ensure perfect matching of the superimposed images, a read/write memory module with image scale variation for transition from small to large images, an image mixing unit, and an image analyzer with a readout device interfaced with a universal computer.

11 Claims, 16 Drawing Figures

FIG.7
FIG.8
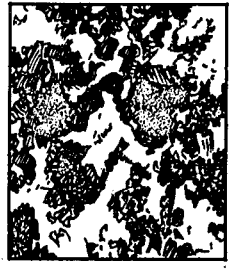
FIG.9
FIG.10
FIG.11

METHOD AND APPARATUS FOR QUANTITATIVE STRUCTURAL ANALYSIS OF SOLIDS

FIELD OF THE INVENTION

1. Background of the Invention

The present invention relates to structural analysis of porous bodies and, more particularly, to a method and an apparatus for quantitative structural analysis of solids.

The invention can most advantageously be used in geology, e.g., in estimating oil, gas and water resources or determining the collecting capacity of rocks, as well as in the manufacture of ceramics, catalysts, sorbents of construction and abrasive materials, in powder metallurgy and other fields.

At present, quantitative structural analysis of porous bodies is carried out either with the aid of classical physical methods on large samples or by analyzing electron micrographs obtained during investigation of a cleaved specimen in a scanning electron microscope.

Determination of parameters of porous bodies on relatively large specimens is an extremely laborious process often involving undesirable destruction of the object under investigation and sometimes it cannot be done at all because of the impossibility of producing a specimen of the required size.

For example, to determine the porosity of disperse rocks by classical methods such as the cutting ring or volumetric method (porosity is calculated after the rocks's specific density and volume mass have been determined), a cylindrical specimen is required 5 cm in diameter and 4 cm high, or a specimen of any shape at least 30 cu.cm in volume (cf. Ye.G.Chapovsky, "Laboratory Studies in Soil Research and Soil Mechanics", "Nedra" Publishers, Moscow, 1975, pp. 21, 23 /in Russian/). Determination of pore distribution by size using the mercury porometry technique gives good results but is laborious, time-consuming and fails to take into account isolated (non-communicating) pores. Determination of perviousness is carried out on standard cylindrical specimens of at least 250 cu.cm in volume. Apart from being laborious and time-consuming, determination of the granulometric composition of a specimen involves destruction of it and its forced dispersion, which introduces uncertainty into the analysis results (cf. Ye.G.Chapovsky, "Laboratory Studies in Soil Research and Soil Mechanics", "Nedra" Publishers, Moscow, 1975, pp. 37-73 /in Russian/).

2. Description of the Prior Art

The prior art methods of determining porosity, involving electron micrography of a specimen's surface with use being made of image analyzers, are inefficient and unreliable because on the micrograph being analyzed a considerable part of the pores may turn out to be imprints of the particles remaining on the mating surface of the cleaved specimen. The use of quantitative data obtained by such a method in geology, for example, in assessing the collecting capacity of oil- and gas-bearing rocks, may be misleading as far as the actual reserves of oil and gas in the field are concerned.

The prior art apparatus for structural analysis of solids, such as "Quantimet-720" (cf. A.K.Terrel, "Automatic Image Analysis by "Quantimet-720" — a New High-Accuracy and Fast-Response System", Proceedings of the All-Union Conference on Automation of Scientific Research, USSR Academy of Science, Siberian Branch, "Nauka" Publishers, Moscow, 1970, pp. 54, 55 /In Russian/), enabling investigation of the structure of a solid with the aid of micrographs of a specimen's surface and determination of total porosity and distribution of pores by size (area, perimeter, etc.), fail, due to the ambiguity of the initial images, to provide reliable data for determining the properties of solids and make it impossible to determine the anisotropy of structure of the pore space.

SUMMARY OF THE INVENTION

It is an object of the present invention to provide a method for quantitative structural analysis of solids, featuring high accuracy and involving relatively small specimens.

Another object of the invention is to provide a method for quantitative structural analysis of solids, involving specimens less than 1 cu.cm in volume.

Still another object of the invention is to provide a method for quantitative structural analysis of solids, ensuring a high-accuracy determination of the porosity and skeleton component of a solid.

Yet another object of the invention is to provide a method for quantitative structural analysis of solids, permitting automation of the process of analysis which is substantially nondestructive testing of the materials of interest.

And, finally, it is an object of the present invention to provide an apparatus ensuring high accuracy of automatic quantitative structural analysis of solids, which would considerably enhance the analysis efficiency in the case of complex structures.

These and other objects are attained by a quantitative structural analysis of solids, whereby a specimen to be examined is cleaved and placed in a scanning electron microscope, and an image thereof is obtained to be quantitatively analyzed according to the invention, the surfaces of the cleaved specimen, conjugate along the plane of division, are scanned, the resulting images are superimposed, and the total image is quantitatively analyzed.

An advantage of the proposed method is that superimposition of the images of the conjugate surfaces, producing a total image and determination of the structure from such a total image permit highly accurate and reliable information on the structure of solids to be obtained, since the superimposition of the images, as has been corroborated by tests and as will be considered in greater detail in what follows, eliminates invalid information on porosity. This is due to the fact that the images of imprints of particles, which may be otherwise interpreted as pores, are compensated for as a result of superimposition, by the images of the particles responsible for these imprints, while only the actual pores remain visible.

The proposed method is applicable for determining not only porosity, but also a skeleton component of the structure (with reference to the size and shape of pores, grains, their distribution by these parameters), determining the physical parameters of all types of pores, calculating the frequency of contacts between particles and determining their type.

The substantially higher, at least tenfold, accuracy of such analysis permits the specimen size to be decreased accordingly, whereby analysis is rendered nondestructive, which is particularly essential in the case of expensive materials and enables coreless drilling of prospecting bore-holes with drill cuttings being used for analysis.

For quantitative determination of porosity, one should preferably obtain, in the scanning electron microscope, negative images of the conjugate specimen cleavage surfaces, superimpose them, and quantitatively determine the parameters of porosity from the total image.

In order to feed porosity data into a computer, i.e., digitize the image, the direction of anisotropy of the pore space is determined by passing a monochromatic light beam through the total image of the conjugate surfaces, and the image is read out in the same direction which is the optimum readout direction.

To investigate a skeleton component of the structure, in the scanning electron microscope, a positive total image is obtained along with negative images of the conjugate cleavage surfaces, which are then superimposed in pairs, total images of grain imprints on the cleavage surfaces are obtained, these images are converted to a contour form, the converted images are superimposed, resulting in a contour image of a granular structure component, and the skeleton component of the structure is quantitatively analyzed. This method permits investigation and obtainment of a full picture of the structure of a solid, including such binding components as cement, glass, etc. To this end, the image of pores, which is a positive total image, is converted to a contour image superimposed on the contour image of the skeleton component and the solid structure is quantitatively analyzed.

For a higher accuracy of matching the images of the conjugate cleavage surfaces and for enhancing certain image areas at higher magnification, consecutive images of the conjugate areas are obtained, from small to high magnification, the first pair of images at minimum magnification being superimposed along the specimen's contour or characteristic morphological features observed on both cleavage surfaces. Then, one of the conjugate images is marked at portions selected for investigation at higher magnification, the marks being transferred on the other conjugate image, the conjugate image areas selected for investigation being detected by way of visual monitoring, with reference being made to the marks on the conjugate images, and brought to the center of the field of vision of the scanning electron microscope, the images being recorded with the marks from the preceding small-magnification image being transferred on the resulding image and with visual monitoring being exercised with reference to morphological features, the conjugate images being matched with reference to the marks, and said operations being repeated each time a greater-magnification image is obtained.

Manual implementation of the proposed method for quantitative structural analysis of solids is a time-consuming and laborious procedure even when instantaneous micrography techniques are used, because of many people being involved in the investigation, preparation of the conjugate specimen cleavage surfaces and their micrography, development of the negatives of the conjugate cleavage surfaces, their matching by salient morphological features, obtaining total negatives, printing of electron micrographs, analysis of porosity with the aid of an image analyzer, obtaining slides (positive images) from the total negatives, their superimposition on the negative images of the conjugate cleavage surfaces, printing electron micrographs from the matched pictures, subsequent quantitative analysis of the grained structure component with the aid of the image analyzer, and so on.

Speeding up of the process of the structural analysis of solids, elimination of numerous manual operations involved in carrying out the above method, elimination of subjective errors inevitable in manual operations and, hence, enhancing the accuracy of the obtained results are made possible with the aid of the proposed apparatus.

The proposed apparatus for quantitative structural analysis of solids comprises a scanning electron microscope with a TV monitor intended for visualization of the image of conjugate cleavage surfaces of the specimens placed in the microscope. The TV monitor is connected to a video recorder of its output signals. The video recorder is, in turn, associated by direct coupling and feedback with a TV monitor with brightness control and a light pen for marking the images on both TV monitors. The TV monitor of the scanning electron microscope is also directly connected to the additional TV monitor with brightness control for simultaneous display on the screen of the latter the image of the conjugate surfaces. There is provided an image mixing unit having its input connected to the output of the TV monitor of the microscope and to the output of the video recorder and associated by direct coupling and feedback with the additional TV monitor with brightness control. The image mixing unit is intended for matching and superimposing images with reference to marks by way of perfect matching of the marks representing clearly defined conjugate points on the images being superimposed. In addition, the image mixing unit is coupled to an analyzer of its output signal, intended for readout and analysis of the total image. The output of the image analyzer is connected to the input of the video recorder and to an electronic computer. Provision is also made in the apparatus for a read/write memory module which is essentially a means for varying the scale of the image on the screen of the associated TV monitor with brightness control. The input of the read/write memory module is connected to the output of the image mixing unit.

BRIEF DESCRIPTION OF THE DRAWINGS

The invention will now be described in greater detail with reference to preferred embodiments thereof, taken in conjunction with the accompanying drawings, wherein:

FIG. 7 is an electron micrograph of a cleavage surface of a specimen with high porosity;

FIG. 8 is an electron micrograph of the specimen cleavage surface conjugate with the surface of FIG. 7;

FIG. 9 is an electron micrograph of the total image of both conjugate cleavage surfaces of the specimen with high porosity;

FIG. 10 is an electron micrograph of grain imprints on the surface shown in FIG. 7;

FIG. 11 is an electron micrograph of grain imprints on the surface shown in FIG. 8;

DESCRIPTION OF THE INVENTION

The proposed method can be realized as follows

A specimen to be investigated is cleaved (fractured) in any known manner into two pieces having conjugate cleavage surfaces.

Figure 1:
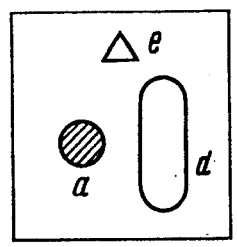
FIG. 1 shows schematically a cleavage surface of a specimen.
Figure 2:
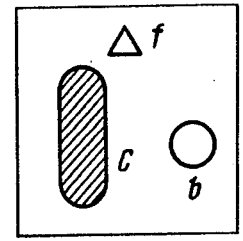
FIG. 2 shows the specimen cleavage surface conjugate with the surface shown in FIG. 1.
Figure 3:
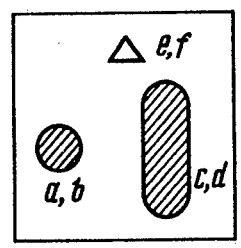
FIG. 3 is a total image of both conjugate specimen cleavage surfaces.

By conjugate surfaces are meant surfaces of two bodies, characterized by concavities and convexities on one surface having respective convexities and concavities on the other surface, perfectly matching in shape, size and location. Thus, any cavities occurring in the plane of division are deviations from conjugation. Mathematically, conjugate surfaces are those described by functions U (x,y,z) and V (x,y,z) and satisfying the following formulae: $dU/dx = dV/dy$; $dU/dy = dV/dx$; $dU/dx = -dV/dz$; $dU/dy = -dV/dz$. Referring now to the drawings, FIG. 1 shows one and FIG. 2 shows the other conjugate surface of the cleaved specimen, in which corresponding to a round particle a (convexity) is, on the conjugate surface, an imprint b (concavity), while corresponding to an elongate particle c (convexity) is an imprint d (concavity); corresponding to a pore e on one surface is a pore f on the other.

The present invention is based on the well known physical phenomenon of optical multiplication or superimposition of images. In the case of multiplication, the transmission factor of the superimposed optical transparencies is equal to the product of transmission factors of each transparency. When images are superimposed and simultaneously projected on the same screen, the brightness at each point of the screen is equal to the sum of brightnesses of each superimposed image (cf. A. Rosenfeld, "Image Identification and Processing", "Mir" Publishers, Moscow, 1972, p. 67 /in Russian/). The procedure of multiplying images is widely used in various photographic processes, particularly, in aerial photography to enhance the quality of irregularly exposed pictures by way of masking (cf. V. Ya. Mikhailov, "The Practice of Using Unsharp Masks in an Inactive Process" in "Geodeziya i kartografiya", No. 1, 1957, pp. 27–32 /in Russian/). Multiplication is achieved by superimposing a transparency of the aerial photograph on a transparency showing the correction mask with the result that the field of the aerial photograph is flattened, and previously unseen features become visible all over the picture. Similar flattening may be achieved by superimposing the aerial photograph and correction mask on a TV screen.

For a better understanding of the proposed method, consider the above procedure as applied to revealing features representative of cavities inside a solid, as well as a skeleton component of the solid's structure, with the aid of electron micrographs of the conjugate specimen cleavage surfaces.

If the solid had no pores, multiplication or superimposition of the images of the conjugate surfaces would result in a field with uniform optical density, because the pictures can be considered as an image-mask pair. Since the solids under investigation are porous, no mutual compensation takes place of the transmission factors or brightness in the porous areas of the conjugate surfaces, and pores manifest themselves as spots against the background of a uniform field. Taken as an example were specimens of two types of solids: those with high porosity (60%) and low porosity (15%).

In the former case, the conjugate surfaces (FIGS. 7 and 8) differ greatly because of the high porosity, and the total image (FIG. 9) clearly shows numerous pores; while in the latter case, the surfaces are almost completely conjugate (FIGS. 4 and 5), and the total image (FIG. 6) shows very few pores.

The procedure of optical multiplication of images permits using the positive image of pores (FIG. 9) as a correction mask to obtain an image of grain imprints on the micrographs of both conjugate surfaces (FIGS. 10 and 11).

Figure 4:
FIG. 4 is an electron micrograph of a cleavage surface of a specimen with low porosity.
Figure 5:
FIG. 5 is an electron micrograph of the specimen cleavage surface conjugate with the surface of FIG. 4.
Figure 6:
FIG. 6 is an electron micrigraph of the total image of both conjugate cleavage surfaces of the specimen with low porosity.
Figure 12:
FIG. 12 is an electron micrograph of a contour image of the granular component of FIG. 10.
Figure 13:
FIG. 13 is an electron micrograph of a contour image of the granular component of FIG. 11.
Figure 14:
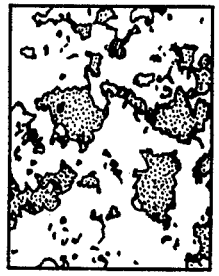
FIG. 14 is an electron micrograph of the total contour image obtained as a result of conversion of the image of FIG. 9.

In order to obtain a contour image of all structural components of the solid, the images of pores (FIG. 9) and grain imprints (FIGS. 10 and 11) are converted to contour forms (FIGS. 12, 13 and 14) by way of high-frequency image filtration mathematically described by differentiation (cf. A. Rosenfeld, "Image Identification and Processing", "Mir" Publishers, Moscow, 1972, pp. 114–123 /in Russian/). Individual contour images of the solid's structural components are superimposed at the same time to obtain a complete structural picture. Further procedure is that both parts of the specimen, having conjugate surfaces, are mounted together on the specimen stage and then placed in the specimen chamber of a scanning electron microscope of any type, e.g., described in the catalogue of "Coates and Welter" ("106A SEM Ultra High Resolution, USA, 4/1/75"). To prevent distortion of the shape of the structural components of the specimen, the specimen is preferably arranged at a right angle to the electron probe. Then, at moderate magnifications (about 100X), both specimen cleavage surfaces are examined with a view to finding conjugate portions thereon. Therewith, reference is made to salient morphological features of the specimen (clearly visible particles, fissures, pores on one cleavage surface and mating pores on the other). An image of the conjugate portions is obtained, they are photographed on a film or a plate, and negatives are produced (photographs made from these negatives are shown in FIGS. 4 and 5). Then, the negative of one conjugate portion is superimposed on that of the other (at a given magnification), both negatives are properly matched, and a total negative is obtained which, when printed, produces a total black-and-white picture (FIG. 6) on which dark spots unambiguously represent pores, while bright spots represent particles. With the aid of any known image analyzer, such as "Quantimet-720", quantitative analysis of the true structure of the specimen's pore space is made. The basic characteristics are, in this case, total porosity as well as distribution of pores by size and depth (the measure of depth is the optical density of a pore's image).

However, structural analysis of solids with the aid of special-purpose image analyzers available at present does not permit determination of certain important physical properties of specimens, such as perviousness, effective porosity, pore tortuosity factor and distribution of hydraulic radii or pores. The use of an electronic computer permits more flexible and complete calculation of the physical properties of solids on the basis of analysis of electron micrographs. Calculations involve appropriate programs written for each particular case, which are not described herein.

For the electron micrograph data to be fed into the computer, they must be read out and digitized. The readout of an image per se is a well known procedure and is carried out with the aid of any of various conventional devices, for example, the widely used fascimile recorder. It has been established, however, that if the anisotropy of a solid's structure is not taken into account, serious errors occur in the course of computation of some parameters, such as perviousness. To determine the optimum image readout direction corresponding to that of anisotropy of the pore space image, the pore space image is transformed to an image of an optical spatial spectrum. For this purpose, a monochromatic light beam is passed through a transparency which is a total image of the conjugate specimen cleavage surfaces, and, with the aid of a focusing lens, the light distribution is registered in the back focal plane to provide for a spatial spectrum of the image. A similar procedure can be carried out by means of optical filters, for example, a commercially produced optical filter of the "Coherent-1" type (cf. "Catalogue of Geophysical Instrumentation", "Nedra" Publishers, Leningrad, 1973 /in Russian/). The resulting image of the optical spectrum is used to define the direction of maximum anisotrophy, and hence, the direction of image readout on the image of pores. The resolution of readout is determined either by the investigation object or by the capacity of the computer'read/write memory. Thus, after the pore image has been read out, it is digitized form a matrix fed into the computer. It should be noted that such digitizing aimed at calculation of the physical properties of solids makes sense only in the context of electron micrographs presenting a true picture of porosity, i.e., pictures obtained by the herein-proposed method, and cannot be applied to analysis of an image of a single specimen cleavage surface because of the initial data being invalid.

Figure 15:
FIG. 15 is an electron micrograph of the total image of the complete specimen's structure.

To determine a skeleton (granular) structure component, basically the same approach is used as in porosity studies, the difference being that after the total negative has been obtained, a slide (positive on film or plate) (FIG. 9) is produced therefrom and superimposed successively on each negative of a respective cleavage surface (similarly to superimposing negatives). As a result, total negatives are obtained, which are then printed to produce micrographs showing grains on respective specimen cleavage surfaces (FIGS. 10 and 11). Image analyzers enable evaluation of grain size, shape and distribution by size. Thereafter, photography, video or difrimoscopy techniques are used to convert the total negative images of grain imprints on each cleavage surface to contour images (FIGS. 12 and 13) which, when superimposed as described above, produce a contour image of the skeleton component of the solid. If the image of the porous component is also converted to a contour image and the contour image is matched with the image of the skeleton component, the resulting image offers a complete picture of the solid's structure (FIG. 15). This picture is used for discrimination of the nodal points of the structure, representative of intergranular contacts, as well as for quantitative analysis of the skeleton component of the structure with the aid of any conventional image analyzer. Considered above were problems related to obtaining a true picture of porosity (total image), however, for more perfect matching of images and enhancing them at higher magnification, one should investigate a specimen in a scanning electron microscope from low to higher magnifications, in which case the first pair of images produced at minimum magnification are superimposed following the specimen's contour or salient morphological features observed on both cleavage surfaces. Then, one of the superimposed images is marked at portions selected for examination at higher magnification. The marks are transferred to the other image. The conjugate portions selected for examination at higher magnification are then detected by way of visual monitoring with reference to the marks on the superimposed images and brought to the center of the field of vision of the microscope. These portions are photographed, and the marks from the previous small-magnification image are transferred to the resulting images, with visual monitoring being exercised with reference to morphological features. The conjugate portions are matched with references to the marks, and each time a higher-magnification image is produced, the above operations are repeated.

Figure 16:
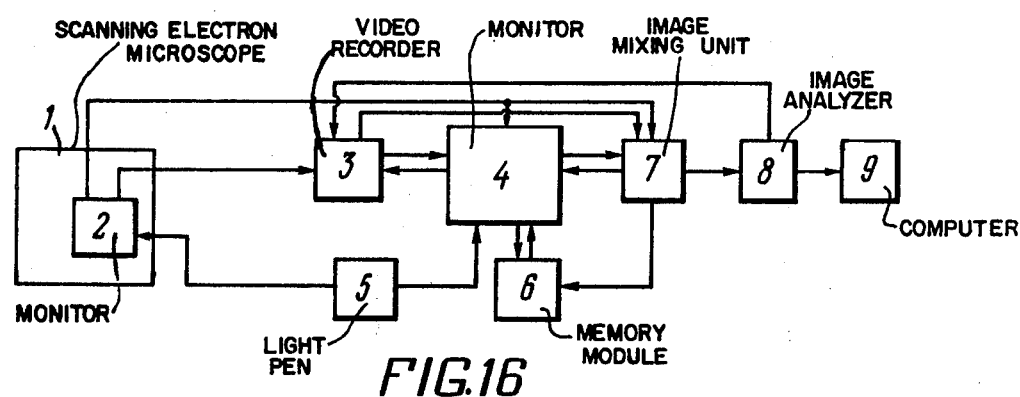
FIG. 16 is a block diagram of an apparatus for carrying out the proposed method.

To speed up the process of structural analysis of solids and eliminate numerous manual operations involved in such analysis, proposed herein is an apparatus whose block diagram is shown in FIG. 16.

The apparatus for quantitative structural analysis of solids, according to the invention, comprises a scanning electron microscope (SEM) 1 which may be of any known type (e.g., SEM "CWIKSCAN-106A", cf. catalogue of "Coates and Welter", "106A SEM Ultra High Resolution, USA, 4/1/75") and provided with a TV monitor 2 for visualization of the image of the surface of a specimen placed on the specimen stage (not shown). The output of the TV monitor 2 is coupled to the input of a video recorder 3 intended for video recording of the image; this unit may be any conventional video recorder (e.g., "Sony AV-3650" manufactured by "Sony" of Japan). The apparatus also comprises an additional TV monitor 4 with brightness control (an "auxiliary TV monitor" manufactured by "Coates and Welter", USA, can be used) associated through direct coupling and feedback with the video recorder. Images on the screen of the TV monitors are marked by means of a light pen 5. There is also provided a read/write memory module 6 enabling the image scale to be varied (e.g., a "CWICKSTOR$^{tm}$ Image Storage System" module) associated by direct coupling and feedback with the additional TV monitor 4. In addition, the apparatus includes an image mixing unit 7 which may be any known mixing unit widely used in television, e.g., a C12-75-2 unit (cf. "Technical Description of Stationary Color TV Unit" "Respublika", USSR, 1975 /In Russian/). Inputs of the image mixing unit 7 are connected to the output of the SEM TV monitor 2 and to the output of the video recorder 3, respectively. The image mixing unit 7 is connected via direct coupling and feedback, to the additional TV monitor 4. The output of the image mixing unit 7 is coupled to the input of the read/write memory module 6 and to the input of an image analyzer 8.

The image mixing unit 7 is intended for matching and superimposition of images with reference to marks representing definite conjugate points of the images being superimposed. The image analyzer 8 (e.g., "Quantimet-720") including a readout device (not shown) has its output connected to an input of an electronic computer 9 and is intended for digitizing images by readout of an image in a predetermined direction, as well as for preliminary quantitative structural analysis of the image. The input of the image analyzer 8 is connected to the input of the video recorder 3 and, via the recorder 3, to the image mixing unit 7.

The apparatus of the present invention operates as follows.

A small-magnification image F of one of the conjugate specimen cleavage surfaces is obtained on the screen of the TV monitor 2 of the scanning electron microscope 1. Primary marks $M_1$ are applied on this image with the aid of the light pen 5 to produce an image $F_{M_1}$ which is fed to the video recorder 3 and displayed on the screen of the additional TV monitor 4. Then, the image F* of the other conjugate surface is produced on the screen of the TV monitor 2 with primary marks also being applied thereon with the aid of the light pen 5, and the resulting image $F*_{M_1}$ is recorded by the video recorder 3. The images $F_{M_1}$ and $F*_{M_1}$ are superimposed with reference to the marks $M_1$ by means of the image mixing unit 7. The result of the superimposition is visualized on the screen on the TV monitor 4 and, at the same time, fed from the image mixing unit 7 to the image mixing unit 7 to the image analyzer 8, and then to the computer for further processing.

Thereafter, applied on the image $F_{M_1}$ displayed on the screen of the TV monitor 3, with the aid of the light pen 5, are secondary marks $M_2$, resulting in an image $F_{M_{1,2}}$ which is recorded by the video recorder 3. This image is fed to the read/write memory module 6 in which it is varied in scale (magnified) to the next required magnification, whereby an image $F''_{M_2}$ is produced. Therewith, the primary marks $M_1$ go beyond the frame of the picture, and displayed on the screen is only the magnified image with the secondary marks $M_2$. Thereafter, produced on the screen of the TV monitor 2 of the scanning electron microscope 1 is an image of the first conjugate specimen cleavage surface on the same scale as the image $F''_{M_2}$ which is then marked with secondary marks by means of the light pen 5, and an image $F''_{M''_2}$ is obtained. This image is recorded by the video recorder 3, then the images $F_{M_{1,2}}$ and $F*_{M_1}$ are called from the video recorder 3 and displayed on the TV monitor 4. By manipulating the brightness control, the image F is removed from the image $F_{M_{1,2}}$ (with only the primary and secondary marks being left), and the remaining primary and secondary marks $M_{1,2}$ are matched, with the aid of the image mixing unit 7, with the image $F*_{M_1}$ to produce a total image of the second conjugate specimen cleavage surface together with the primary and transferred secondary marks. By means of the read/write memory module 6, this image is magnified to an image $F*'''_{M_2}$. Displayed on the screen of the TV monitor 2 of the scanning electron microscope 1 is an image of the second conjugate surface of the same scale, and the secondary marks from the image $F*''_{M_2}$ are transferred thereto with the aid of the light pen 5 and by way of visual monitoring on the screen of the TV monitor 4, as a result of which an image $F*''_{M''_2}$ is obtained. Then, with the aid of the image mixing unit 7, the images $F''_{M''_2}$ and $F*''_{M''_2}$ are superimposed, and a total image is obtained, which is displayed on the screen of the TV monitor 4 and fed to the image analyzer 8; this sequence is repeated for each new manigification and for new marks.

From the image analyzer 8, data pertaining to each image is fed into the computer 9, wherein the parameters of the solid's pore space are fully calculated with the aid of programs which are written for each specific task and which are not described here.

In structural skeleton component investigation, individual images of conjugate cleavage surfaces (FIGS. 7 and 8) and the corresponding pore images (FIG. 9) available in the video recorder 3 are fed to the image mixing unit in which, for each magnification and each pair of images of the conjugate surfaces (FIGS. 7 and 8), the corresponding pore images (FIG. 9) are superimposed with the result a half-tone picture of the granular structure components (FIGS. 10 and 11) are produced, which, just as in the case of pore images, are converted to a contour form (FIGS. 12 to 14) with the aid of the image analyzer 8 and fed, via the video recorder 3, to the image mixing unit 7 wherein they are superimposed. Thus, a complete contour image of the solid's structure (FIG. 15) is obtained This image is first analyzed by the image analyzer 8 and then, according to a respective program, by the computer 9.

The advantage of the present invention is that it enables the accuracy of determining parameters of solids to be increased several-fold, at least by one order of magnitude, as well as permits automation of the process of structural anaylsis of solids, which, in turn, substantially improves the efficiency of investigation and provides rapid solution to problems arising in connection with the structure of solids.

While we have shown and described the preferred embodiments of the present invention by way of ilustration, it is to be understood by those skilled in the art that many modifications thereof may occur without departing from the true spirit and scope of the invention.

What is claimed is:

1. A method for quantitative structural analysis of solids, comprising the following steps: (a) cleaving a specimen; (b) placing both parts of the cleaved specimen in a scanning electron microscope and scanning the conjugate cleavage surfaces to obtain images thereof; (c) superimposition of the resulting images of said conjugate surfaces; and (d) analysis of the superimposed images to determine structural parameters of said specimen.

2. A method as claimed in claim 1, wherein negative images of the conjugate cleavage surfaces are obtained in the scanning electron microscope, and the resulting total negative image is used for quantitative analysis of porosity.

3. A method as claimed in claim 1, wherein for to feeding data into an electronic computer, the image is read out by a digitizer and, for determining the readout direction, a monochromatic light beam is passed through the total image to obtain an image of a spatial spectrum required to determine the direction of anisotropy of the pore space represented in the image, said direction corresponding to the optimum readout direction.

4. A method as claimed in claim 1, wherein a positive total image is obtained along with negative images of the conjugate cleavage surfaces, said images are superimposed in pairs, and total images are obtained of grain imprints on the cleavage surfaces, the images of the structure components being converted to a contour form, the converted images being superimposed, resulting in a contour image of a granular structure component, and the skeleton component of the structure being quantitatively analyzed.

5. A method for quantitative structural analysis of solids, comprising the following steps: (a) cleaving a specimen; (b) placing both parts of the cleaved specimen in a scanning electron microscope and scanning the conjugate cleavage surfaces to obtain images thereof, first an image of the conjugate surfaces at a relatively small magnification being obtained and then images with relatively high magnification; (c) superimposition of the resulting images of the same magnification; and (d) analysis of the superimposed images to determine structural parameters of said specimen, the resolution of analysis gradually increasing.

6. A method as claimed in claim 5, wherein, after an image at small magnification has been obtained, consecutive images of certain conjugate areas are obtained at magnifications varying from low to high for perfect matching of the images of the conjugate cleavage surfaces of the specimen and for enhancing said image areas at high magnification, the first pair of images at minimum magnification being superimposed along the specimen's contour or characteristic morphological features observed on both cleavage surfaces, one of the conjugate images being marked at portions selected for investigation at higher magnification, the marks being transferred onto the other one of the conjugate images, the conjugate image areas selected for investigation being detected by way of visual monitoring, with reference being made to the marks on the conjugate images, and brought to the center of the field of vision of the scanning electron microscope, said images being recorded with the marks from the preceding small-magnification image being transferred on the resulting images and with visual monitoring being exercised with reference to morphological features, the conjugate images being matched with reference to the marks, and said steps being repeated each time a greater-magnification image is obtained.

7. An apparatus for quantitative structural analysis of solids by superimposition of images of conjugate surfaces, comprising a scanning electron microscope with a TV monitor for visualization of the images of the conjugate cleavage surfaces of specimens placed in said microscope for scanning, a video recorder having a first input connected to a first output of the TV monitor for recording the scanning signals; an additional TV monitor with brightness control having a first output, a first input and a second input respectively electrically associated with a second input and a first output of said video recorder and with a second output of the TV monitor of said scanning electron microscope for a total image of both conjugate specimen cleavage surfaces to be displayed on the screen of said additional TV monitor; a light pen for marking images on the screens of both monitors; an image mixing unit having a first input and a first output connected, respectively, to a second output and a third input of the additional TV monitor and having second and third inputs respectively connected to the second output of the TV monitor of the scanning electron microscope and to a second output signal from the video recorder for matching and superimposing images with reference to marks for perfect matching of the marks representing clearly defined conjugate points on the images being superimposed.

8. An apparatus as claimed in claim 7, further comprising an analyzer of an output signal of said image fixing unit coupled to a second output of the image fixing unit for analysis of the total image and data input in an electronic computer.

9. An apparatus as claimed in claim 8, wherein the output signal from the image analyzer is applied to a third input of the video recorder.

10. An apparatus as claimed in claim 7, wherein a third output of the additional TV monitor with brightness control is connected to a means for varying the scale of the image on its screen, said means being essentially a read/write memory module associated through direct coupling and feedback with the third output of said additional TV monitor for storing the scale of a preceding image and further magnification thereof.

11. An apparatus as claimed in claim 10, wherein a third output of the image mixing unit is connected to an input of the read/write memory module for storing and varying the image scale.

* * * * *